United States Patent
Kim et al.

(10) Patent No.: US 9,186,415 B2
(45) Date of Patent: Nov. 17, 2015

(54) LONG-ACTING HUMAN FOLLICLE-STIMULATING HORMONE FORMULATION USING IMMUNOGLOBULIN FRAGMENT

(75) Inventors: Chang Hwan Kim, Suwon-si (KR); Sung Kap Hong, Yongin-si (KR); Byung Sun Lee, Seoul (KR); Soo Young Kwak, Seoul (KR); Mi Ji Lee, Incheon (KR); In Young Choi, Yongin-si (KR); Se Chang Kwon, Seoul (KR)

(73) Assignee: HANMI SCIENCE CO., LTD, Hwaseong-si (KR)

( * ) Notice: Subject to any disclaimer, the term of this patent is extended or adjusted under 35 U.S.C. 154(b) by 78 days.

(21) Appl. No.: 13/638,860

(22) PCT Filed: Apr. 4, 2011

(86) PCT No.: PCT/KR2011/002332
§ 371 (c)(1),
(2), (4) Date: Oct. 1, 2012

(87) PCT Pub. No.: WO2011/122922
PCT Pub. Date: Oct. 6, 2011

(65) Prior Publication Data
US 2013/0022626 A1    Jan. 24, 2013

(30) Foreign Application Priority Data

Apr. 2, 2010  (KR) .................. 10-2010-0030574

(51) Int. Cl.
| | | |
|---|---|---|
| *A61K 38/24* | (2006.01) | |
| *A61K 38/00* | (2006.01) | |
| *A61K 38/16* | (2006.01) | |
| *C07K 16/00* | (2006.01) | |
| *C07K 1/00* | (2006.01) | |
| *A61K 47/48* | (2006.01) | |

(52) U.S. Cl.
CPC ..... *A61K 47/48215* (2013.01); *A61K 47/48369* (2013.01)

(58) Field of Classification Search
None
See application file for complete search history.

(56) References Cited

U.S. PATENT DOCUMENTS

| 5,585,345 | A | 12/1996 | Boime | |
|---|---|---|---|---|
| 6,660,843 | B1 | 12/2003 | Feige et al. | |
| 7,601,516 | B2 * | 10/2009 | Low | 435/69.7 |
| 2004/0023848 | A1 * | 2/2004 | Boehm | 514/2 |
| 2007/0041967 | A1 * | 2/2007 | Jung et al. | 424/133.1 |

FOREIGN PATENT DOCUMENTS

| KR | 10-2002-0081273 A | 10/2002 |
|---|---|---|
| KR | 10-2005-0047032 A | 5/2005 |
| WO | 2005/020934 A2 | 3/2005 |
| WO | 2005/047336 A | 5/2005 |
| WO | 2009/098318 A1 | 8/2009 |

OTHER PUBLICATIONS

Korean Patent Office, Korean Office Action issued in corresponding KR Application No. 10-2011-0030867, dated Feb. 18, 2013.
Duijkers et al., "Single Dose Pharmacokinetics and Effects on Follicular Growth and Serum Hormones of a Long-Acting Recombinant FSH Preparation (FSH-CTP) in Healthy Pituitary-Suppressed Females," Human Reproduction, 2002, vol. 17, No. 8, pp. 1987-1993.
Olijve et al., "Molecular Biology and Biochemistry of Human Recombinant Follicle Stimulating Hormone (Puregon®)," Molecular Human Reproduction, 1996, vol. 2, No. 5, pp. 372-382.
Andrew P. Chapman, "PEGylated Antibodies and Antibody Fragments for Improved Therapy: A Review," Advanced Drug Delivery Reviews, 2002, vol. 54, pp. 531-545.
Veronese et al., "PEGylation, Successful Approach to Drug Delivery," DDT, 2005, vol. 10, No. 21, pp. 1451-1458.
Roberts et al., "Chemistry for Peptide and Protein PEGylation," Advanced Drug Delivery Reviews, 2002, vol. 54, pp. 459-476.
Taiwanese Patent Office, Taiwanese Office Action issued in corresponding TW Application No. 100111783, dated Mar. 20, 2013.
Japanese Patent Office, Japanese Office Action issued in corresponding JP Application No. 2013-502500, dated Feb. 4, 2014.

* cited by examiner

*Primary Examiner* — Shulamith H Shafer
(74) *Attorney, Agent, or Firm* — Sughrue Mion, PLLC

(57) ABSTRACT

The present invention relates to a long-acting human follicle-stimulating hormone formulation having improved in vivo duration and stability, comprising a human follicle-stimulating hormone conjugate that is prepared by covalently linking human follicle-stimulating hormone with an immunoglobulin Fc region via a non-peptidyl polymer, and a preparation method thereof. The long-acting human follicle-stimulating hormone formulation of the present invention maintains in vivo activity of human follicle-stimulating hormone at a relatively high level and remarkably increases the serum half-life thereof.

19 Claims, 10 Drawing Sheets

Figure 5
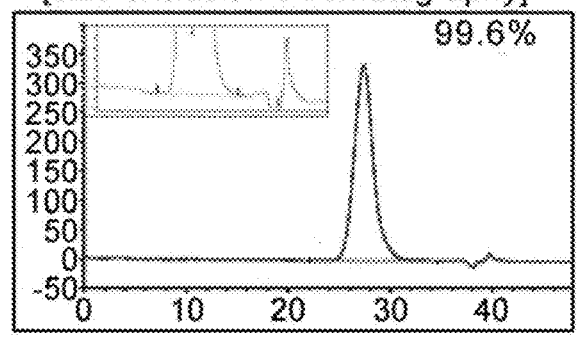
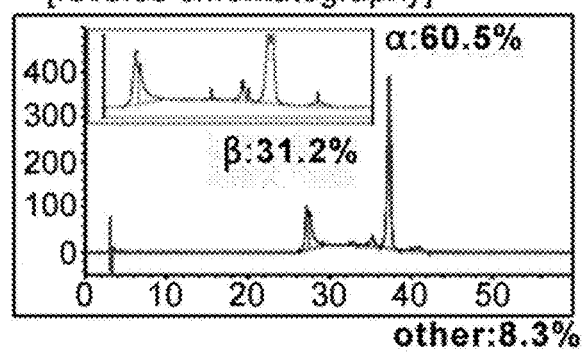
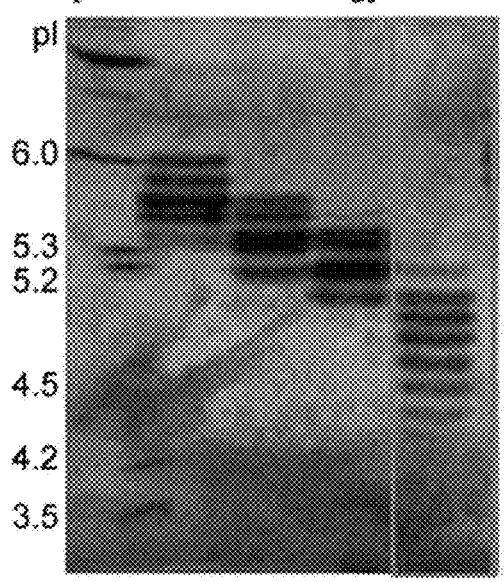

Figure 9
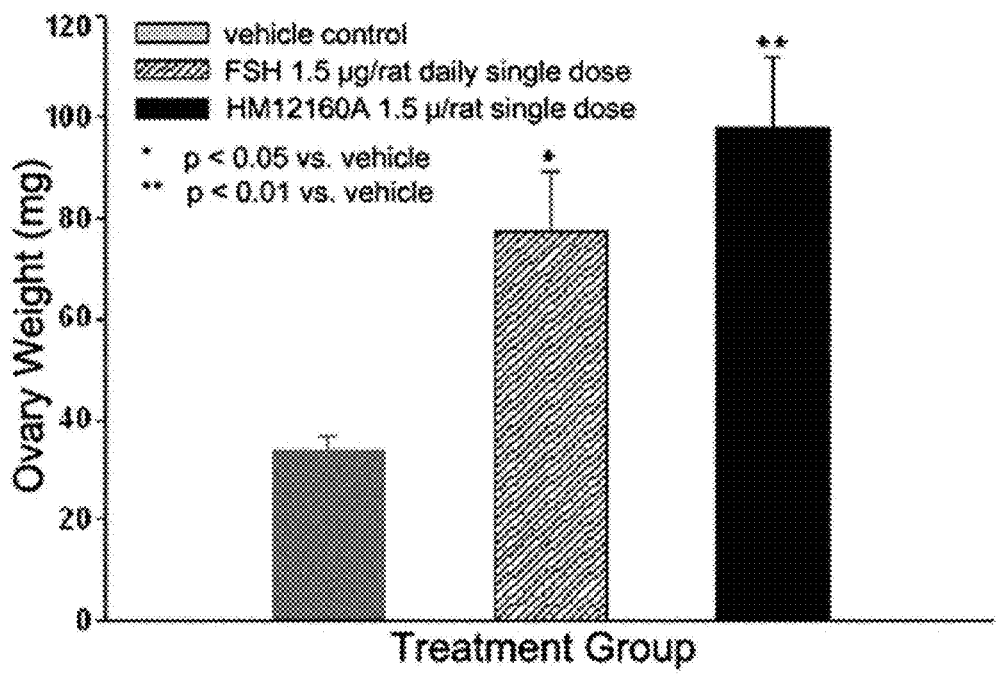
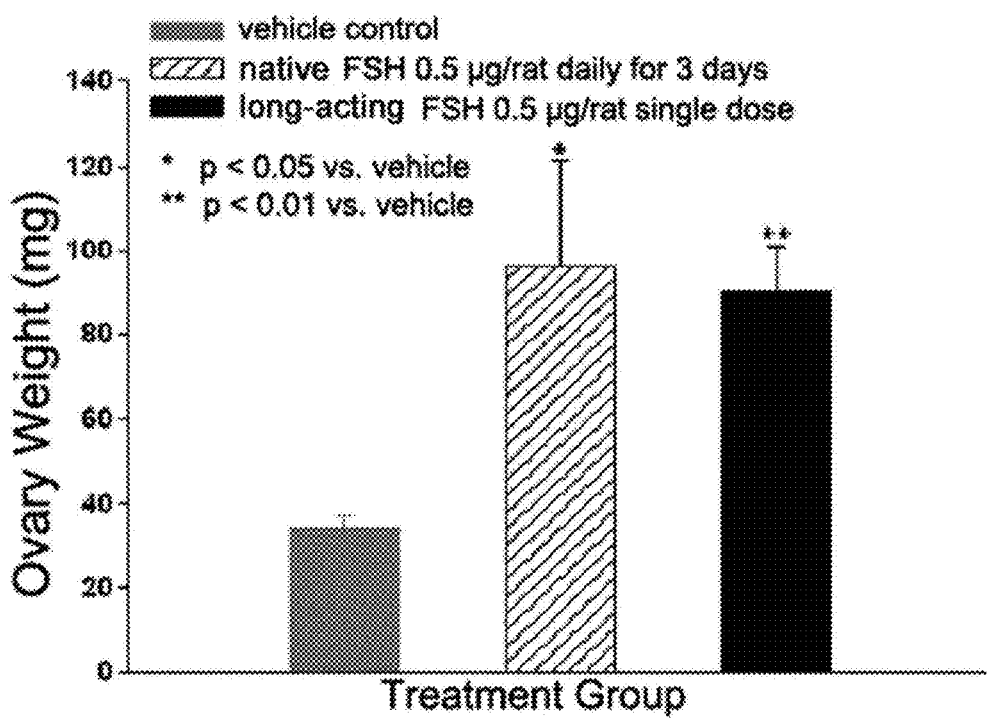

SEQUENCE LISTING

<160> NUMBER OF SEQ ID NOS: 2

<210> SEQ ID NO 1
<211> LENGTH: 92
<212> TYPE: PRT
<213> ORGANISM: Homo sapiens

<400> SEQUENCE: 1

```
Ala Pro Asp Val Gln Asp Cys Pro Glu Cys Thr Leu Gln Glu Asn Pro
 1               5                  10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60
```

```
Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 2
<211> LENGTH: 111
<212> TYPE: PRT
<213> ORGANISM: Homo sapiens

<400> SEQUENCE: 2

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
                20                  25                  30

Tyr Thr Arg Asp Leu Val Tyr Lys Asp Pro Ala Arg Pro Lys Ile Gln
            35                  40                  45

Lys Thr Cys Thr Phe Lys Glu Leu Val Tyr Glu Thr Val Arg Val Pro
        50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110
```

LONG-ACTING HUMAN FOLLICLE-STIMULATING HORMONE FORMULATION USING IMMUNOGLOBULIN FRAGMENT

CROSS REFERENCE TO RELATED APPLICATIONS

This application is a National Stage of International Application No. PCT/KR2011/002332, filed on Apr. 4, 2011, which claims priority from Korean Patent Application No. 10-2010-0030574, filed on Apr. 2, 2010, the contents of all of which are incorporated herein by reference in their entirety.

TECHNICAL FIELD

The present invention relates to a long-acting human follicle-stimulating hormone formulation having improved in vivo duration and stability comprising a human follicle-stimulating hormone conjugate, and a preparation method thereof. The invention provides method for increasing fertility in a subject or a method for treating a subject having a reproduction disorder, such as infertility.

BACKGROUND ART

Infertility is the failure of a couple to conceive a pregnancy after regular sexual intercourse over a given period of time, typically one year, but in some cases 2-3 years. On average, 85% of married couples will have a pregnancy in one year, and a study showed that 25% conceived within 1 month, 70% within 6 months, and 85% within 1 year. After fertility reaches its peak at about the age of 24 in both men and women, the time to conception increases two-fold for every five years they get older. Fertility sharply diminishes from about the age of 35.

The causes of infertility can involve one or both partners. When the problem exists within the male partner, it is referred to as male infertility, and within the female partner, it is referred to as female infertility. According to statistics, male or female infertility accounts for 70% of all infertility cases. Approximately 20% of them are caused by a mix of male and female factors, and approximately 10-15% of them by unknown factors.

The global infertility treatment market exceeded one billion dollars in 2006, and the annual growth rate was around 6%, and it is expected to exceed 1.2 billion dollars in 2011. In Korea, the market sharply increased from 9 billion won in 2006 to 12 billion won in 2007, and a remarkable growth is expected in the coming five years.

A fertility drug is also called an ovulatory stimulant, which is represented by human follicle-stimulating hormone. Human follicle-stimulating hormone is a glycoprotein hormone that is produced by the pituitary gland and released into the endocrine system, and consists of non-covalently linked alpha- and beta-subunits that have 92 and 111 amino acids, respectively, and there are two asparagines-linked carbohydrate chains on each subunit (Mol Hum Reprod, 1996; 2(5): 371-382).

Insufficient production or secretion of follicle-stimulating hormone fails to induce ovulation, leading to infertility in women, and also fails to produce an adequate number of sperms, leading to infertility in men. Therefore, follicle-stimulating hormone has been used for the treatment of infertility, and it was isolated and purified from the urine of women at first. Like other protein drugs, 80% or more thereof have been currently replaced with recombinant products because of safety concerns. The recombinant products are represented by 'Gonal-F' of Merck-Serono (MSD), 'Puregon' of Organon, etc.

It has been known that ovulation disorders and tubal blockage account for 35%, endometriosis accounts for 20%, and unknown factors account for 10% of female infertility. Assisted reproductive technology, including in-vitro fertilization embryo transfer (IVF-ET), gamete intrafallopian transfer (GIFT), zygote intrafallopian transfer (ZIFT), and intra-cytoplasmic sperm injection (ICSI), have been used for the treatment of female infertility. These procedures require ovulation induction, which is performed by the use of human follicle-stimulating hormone. This hormone is also used for anovulatory women. The causes of male infertility are largely divided into sperm disorders and anatomical abnormalities, and the low sperm count can be treated with the use of human follicle-stimulating hormone.

In the treatment of female infertility by assisted reproductive technology, FSH is usually given at an initial dose of 150 IU-225 IU up to 450 IU once a day, on day 2 or 3 of the ovulation cycle, for 5 days up to 20 days until follicle development is adequate. In the treatment of anovulation, FSH is usually given at an initial dose of 75-150 IU, and if necessary, at a dose of 37.5 IU or 75 IU up to 225 IU once a day at 7 or 14 day intervals for up to 4 weeks. In the treatment of male infertility, FSH is usually given at a dose of 150 IU up to 300 IU three times a week for up to 18 months.

As compared to urine-derived human follicle-stimulating hormone, recombinant human follicle-stimulating hormone currently used is improved in terms of purification yield and stability of supply, especially in terms of safety. However, it is still disadvantageous in that patients should be given treatment for ten consecutive days during a treatment period, and infertile male patients should be treated for up to 18 months, imposing a high economic burden on the patients. Such infertility treatments should be continued in both men and women until a successful pregnancy is achieved. Therefore, it is important to reduce the treatment frequency in terms of patient's convenience and cost reduction, and there is an urgent need to develop long-acting products, similar to the strategies for the development of other protein drugs.

By this demand, studies on long-acting products have been conducted to develop hyperglycosylated FSH (MerckSerono) and CTP (carboxy terminal peptide)-attached FSH-CTP formulation (Schering-plough), which are currently under clinical trials. Of them, hyperglycosylated FSH was prepared by the substitution of the relevant amino acid residues in order to increase the half-life of native FSH (WO-2005020934), and is currently under phase II clinical trial. However, it has been reported that the resulting increase in half-life is less than 2-fold, being shorter than that of FSH-CTP (corifollitropin alfa), and immunological problems are also generated due to modification of amino acids. FSH-CTP (U.S. Pat. No. 5,585,345) was prepared by linking the N-terminal peptide of FSH beta subunit with the C-terminal peptide of the beta subunit of human chorionic gonadotropin, which is one of the gonadotropic hormones. The CTP unit contains four glycosylation sites at the serine residues to remarkably increase the serum half-life of hCG, compared to FSH (Hum Reprod, 2002; 17(8): 1987-1993). At present, FSH-CTP is under schering-plough's phase III clinical trial, and its efficacy on the assisted reproduction program for female patients was known to be similar to that of FSH. Reportedly, the pregnancy rates of native and long-acting forms were about 38%, and FSH-CTP can be prepared as a once-a-week formulation. As described above, follicle development usually takes 10 days, even though there are differences between patients. Thus, additional treatment of native FSH may be required when an assisted reproduction program is conducted using the once-a-week formulation. Further, the initial dose of FSH-CTP exceeds the total dose of native FSH given for one week, which may increase the risk of side-effects such as ovarian hyper-stimulation syndrome.

DISCLOSURE

Technical Problem

In this regard, leading to the present invention, intensive and through research into the development of a method capable of simultaneously maximizing the serum half-life and in vivo activity of human follicle-stimulating hormone resulted in the finding that an immunoglobulin Fc region, a non-peptidyl polymer having two or three reactive terminal groups, and follicle-stimulating hormone are covalently linked to each other at the N-terminus or site-selectively at amino acid residues other than the N-terminus, so as to remarkably prolong in vivo efficacy of the conjugate.

Technical Solution

It is an object of the present invention to provide a long-acting human follicle-stimulating hormone formulation which maintains in vivo activity of human follicle-stimulating hormone and remarkably prolongs the serum half-life thereof at the same time, and a preparation method thereof.

Advantageous Effects

The human follicle-stimulating hormone conjugate of the present invention maintains in vivo activity of glycoprotein at a relatively high level and remarkably increases the serum half-life thereof.

DESCRIPTION OF DRAWINGS

FIG. 5 is the results of size-exclusion chromatography, reverse chromatography, and isoelectric focusing gel electrophoresis of the purified human FSH;

FIG. 9 is the result of comparison of in vivo efficacy between long-acting human FSH and native human FSH;

BEST MODE

Figure 1:
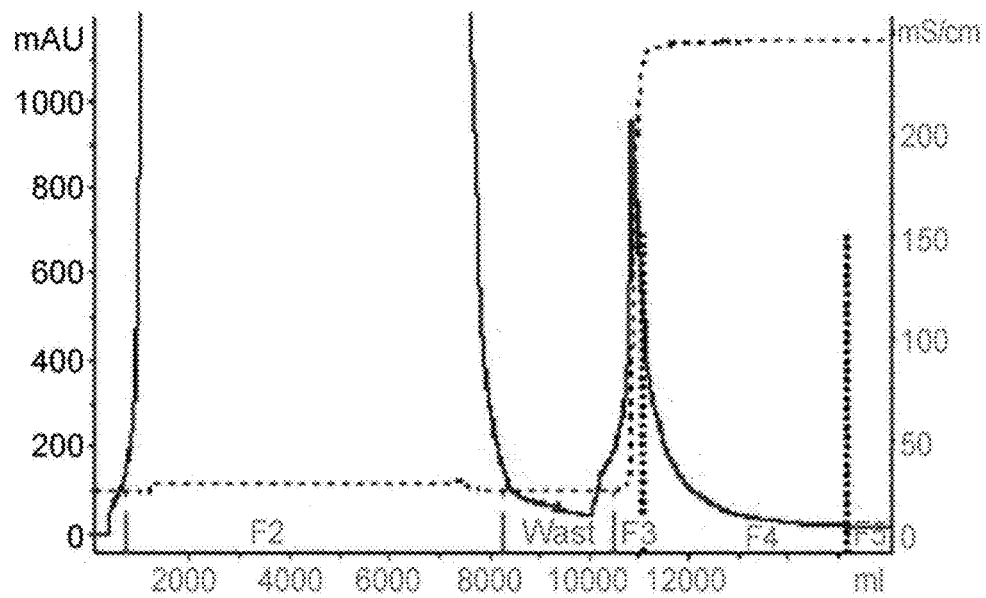
FIG. 1 is the result of dye affinity chromatography for the purification of human FSH.

In one aspect to achieve the above objects, the present invention provides a long-acting human follicle-stimulating hormone formulation having improved in vivo duration and stability, comprising a human follicle-stimulating hormone conjugate that is prepared by covalently linking human follicle-stimulating hormone with an immunoglobulin Fc region via a non-peptidyl polymer having two or three reactive terminal groups.

The human follicle-stimulating hormone used in the present invention is a glycoprotein hormone that is produced by the pituitary gland and released into the endocrine system, and functions to stimulate ovarian follicular production, development, and maturation. Amino acid sequences of the alpha and beta subunits are as follow:

```
Alpha subunit
                                            (SEQ ID NO. 1)
APDVQDCPECTLQENPFFSQPGAPILQCMGCCFSRAYPTPLRSKKTM
LVQKNVTSESTCCVAKSYNRVTVMGGFKVENHTACECSTCYYHKS Beta subunit
                                            (SEQ ID NO. 2)
NSCELTNITIAIEKEECRFCISINTTWCAGYCYTRDLVYKDPARPKI
QKTCTFKELVYETVEVPGCAHHADSLYTYPVATQCECGKCDSDSTDC
TVRGLGPSYCSFGEMKE
```

In a specific embodiment, the human follicle-stimulating hormone used in the present invention can be produced by a recombinant protein production method using animal cells.

Further, the human follicle-stimulating hormone of the present invention is able to bind to the non-peptidyl polymer on various sites. For example, the aldehyde reactive group selectively binds to an N-terminus at a low pH, and can bind to a lysine residue to form a covalent bond at a high pH, such as pH 9.0. A pegylation reaction is allowed to proceed with varying pH, and then a positional isomer can be separated from the reaction mixture using an ion exchange column.

If it is to be coupled at a site other than the N-terminus, a reactive thiol group can be introduced to the site of amino acid residue to be modified in the native amino acid sequence to form a covalent bond using a maleimide linker at the non-peptidyl polymer.

When the aldehyde linker at the non-peptidyl polymer is used, it is reacted with an amine group at the N-terminus and the lysine residue, and a modified form of human follicle-stimulating hormone can be used to selectively increase the reaction yield. For example, only one amine group to be reacted can be retained on a desired site using an N-terminus blocking method, a lysine residue substituting method, a method for introducing an amine group at a carboxyl terminus, or the like, thereby increasing the yield of pegylation and coupling reactions. The methods for protecting the N-terminus include dimethylation, as well as methylation, deamination, acetylation, etc., but are not limited to such alkylation methods.

In the preferred embodiment of the present invention, the human follicle-stimulating hormone conjugate of the present invention is a human follicle-stimulating hormone conjugate, in which an immunoglobulin Fc region specifically binds to the N-terminus of the follicle-stimulating hormone. The N-terminus of alpha- and beta-subunits of human follicle-stimulating hormone is not involved in bonding with receptors. In the present invention, therefore, the Fc region specifically binds to the N-terminus of human follicle-stimulating hormone, thereby maintaining the activity of human follicle-stimulating hormone and also increasing in vivo half-life thereof.

The term "activity", as used herein, means that human follicle-stimulating hormone exhibits its action through binding to the human follicle-stimulating hormone receptor.

Such N-terminus-specific conjugation can be achieved by pH control, and preferably, in the range from 4.5 to 7.0.

The term "N-terminus", as used herein, can be used interchangeably with "N-terminal region".

In one specific embodiment, in the case of using a non-peptidyl polymer having two reactive terminal groups, the present inventors induced an N-terminal pegylation of a native human follicle-stimulating hormone at pH 6.0, to selectively couple PEG to the N-terminus of human follicle-stimulating hormone. Alternatively, in the case of using a non-peptidyl polymer having three reactive terminal groups, the reaction was induced at pH 6.0 by varying the molar ratio to couple PEG to human follicle-stimulating hormone. As compared to the use of a non-peptidyl polymer having two reactive terminal groups, the use of non-peptidyl polymer having three reactive terminal groups may reduce the use of PEG, leading to increased yields.

The immunoglobulin Fc region is safe for use as a drug carrier because it is a biodegradable polypeptide that is in vivo metabolized. Also, the immunoglobulin Fc region has a relatively low molecular weight, as compared to the whole immunoglobulin molecules, and thus it is advantageous in the preparation, purification and yield of the conjugate. The immunoglobulin Fc region does not contain a Fab fragment, which is highly non-homogenous due to different amino acid sequences according to the antibody subclasses, and thus it can be expected that the immunoglobulin Fc region may greatly increase the homogeneity of substances and be less antigenic.

The term "immunoglobulin Fc region", as used herein, refers to a protein that contains the heavy-chain constant region 2 (CH2) and the heavy-chain constant region 3 (CH3) of an immunoglobulin, excluding the variable regions of the heavy and light chains, the heavy-chain constant region 1 (CH1) and the light-chain constant region 1 (CL1) of the immunoglobulin. It may further include a hinge region at the heavy-chain constant region. Also, the immunoglobulin Fc region of the present invention may contain a part or all of the Fc region including the heavy-chain constant region 1 (CH1) and/or the light-chain constant region 1 (CL1), except for the variable regions of the heavy and light chains, as long as it has a physiological function substantially similar to or better than the native protein. Also, it may be a fragment having a deletion in a relatively long portion of the amino acid sequence of CH2 and/or CH3. That is, the immunoglobulin Fc region of the present invention may comprise 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region. Further, the immunoglobulin Fc region of the present invention includes a sequence derivative (mutant) thereof as well as a native amino acid sequence. An amino acid sequence derivative has a sequence that is different from the native amino acid sequence due to a deletion, an insertion, a non-conservative or conservative substitution or combinations thereof of one or more amino acid residues. For example, in an IgG Fc, amino acid residues known to be important in binding, at positions 214 to 238, 297 to 299, 318 to 322, or 327 to 331, may be used as a suitable target for modification. In addition, other various derivatives are possible, including derivatives having a deletion of a region capable of forming a disulfide bond, a deletion of several amino acid residues at the N-terminus of a native Fc form, or an addition of methionine residue to the N-terminus of a native Fc form. Furthermore, to remove effector functions, a deletion may occur in a complement-binding site, such as a C1q-binding site and an ADCC site. Techniques of preparing such sequence derivatives of the immunoglobulin Fc region are disclosed in WO 97/34631 and WO 96/32478. Amino acid exchanges in proteins and peptides, which do not generally alter the activity of the proteins or peptides, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly, in both directions.

The Fc region, if desired, may be modified by phosphorylation, sulfation, acrylation, glycosylation, methylation, farnesylation, acetylation, amidation, and the like.

The aforementioned Fc derivatives are derivatives that have a biological activity identical to that of the Fc region of the present invention or improved structural stability, for example, against heat, pH, or the like.

In addition, these Fc regions may be obtained from native forms isolated from humans and other animals including cows, goats, swine, mice, rabbits, hamsters, rats and guinea pigs, or may be recombinants or derivatives thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)2 fragments. These fragments may be subjected, for example, to size-exclusion chromatography to isolate Fc or pF'c.

Preferably, a human-derived Fc region is a recombinant immunoglobulin Fc region that is obtained from a microorganism.

In addition, the immunoglobulin Fc region of the present invention may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc region results in a sharp decrease in binding affinity to the complement (c1q) and a decrease or loss in antibody-dependent cell-mediated cytotoxicity or complement-dependent cytotoxicity, thereby not inducing unnecessary immune responses in-vivo. In this regard, an immunoglobulin Fc region in a deglycosylated or aglycosylated form may be more suitable to the object of the present invention as a drug carrier.

The term "deglycosylation", as used herein, means to enzymatically remove sugar moieties from an Fc region, and the term "aglycosylation" means that an Fc region is produced in an unglycosylated form by a prokaryote, preferably *E. coli*.

In addition, the immunoglobulin Fc region may be an Fc region that is derived from IgG, IgA, IgD, IgE and IgM, or that is made by combinations thereof or hybrids thereof. Preferably, it is derived from IgG or IgM, which is among the most abundant proteins in the human blood, and most preferably from IgG, which is known to enhance the half-life of ligand-binding proteins.

The term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

The term "hybrid", as used herein, means that sequences encoding two or more immunoglobulin Fc regions of different origin are present in a single-chain immunoglobulin Fc region. In the present invention, various types of hybrids are possible. That is, domain hybrids may be composed of one to four domains selected from the group consisting of CH1, CH2, CH3 and CH4 of IgG Fc, IgM Fc, IgA Fc, IgE Fc and IgD Fc, and may include the hinge region.

On the other hand, IgG is divided into IgG1, IgG2, IgG3 and IgG4 subclasses, and the present invention includes combinations or hybrids thereof. Preferred are the IgG2 and IgG4 subclasses, and most preferred is the Fc region of IgG4 rarely having effector functions such as CDC (complement dependent cytotoxicity). As the drug carrier of the present invention, the most preferable immunoglobulin Fc region is a human IgG4-derived non-glycosylated Fc region. The human-derived Fc region is more preferable than a non-human derived Fc region, which may act as an antigen in the human body and cause undesirable immune responses such as the production of a new antibody against the antigen.

The term "non-peptidyl polymer", as used herein, refers to a biocompatible polymer including two or more repeating units linked to each other by any covalent bond excluding a peptide bond.

The non-peptidyl polymer which can be used in the present invention may be selected form the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (poly(lactic acid)) and PLGA (polylactic-glycolic acid), lipid polymers, chitins, hyaluronic acid, and combinations thereof, and preferably, polyethylene glycol. The derivatives thereof well known in the art and being easily prepared within the skill of the art are also included in the scope of the present invention.

The peptide linker which is used in the fusion protein obtained by a conventional inframe fusion method has drawbacks in that it is easily in-vivo cleaved by a proteolytic enzyme, and thus a sufficient effect of increasing the serum half-life of the active drug by a carrier cannot be obtained as expected. However, in the present invention, the polymer having resistance to the proteolytic enzyme can be used to maintain the serum half-life of the peptide being similar to that of the carrier. Therefore, any non-peptidyl polymer can be used without any limitation, as long as it is a polymer having the aforementioned function, that is, a polymer having resistance to the in-vivo proteolytic enzyme. The non-peptidyl polymer has a molecular weight in the range of 1 to 100 kDa, and preferably of 1 to 20 kDa. The non-peptidyl polymer of the present invention, linked to the immunoglobulin Fc region, may be one polymer or a combination of different types of polymers.

The non-peptidyl polymer used in the present invention has a reactive group capable of binding to the immunoglobulin Fc region and protein drug.

The non-peptidyl polymer has a reactive group at both ends, which is preferably selected from the group consisting of a reactive aldehyde group, a propionaldehyde group, a butyraldehyde group, a maleimide group and a succinimide derivative. The succinimide derivative may be succinimidyl propionate, hydroxy succinimidyl, succinimidyl carboxymethyl, or succinimidyl carbonate. In particular, when the non-peptidyl polymer has a reactive aldehyde group as two or three reactive terminal groups, it is effective in linking at both ends with a physiologically active polypeptide and an immunoglobulin with minimal non-specific reactions. A final product generated by reductive alkylation by an aldehyde bond is much more stable than that linked by an amide bond. The aldehyde reactive group selectively binds to an N-terminus at a low pH, and binds to a lysine residue to form a covalent bond at a high pH, such as pH 9.0.

The two or three reactive terminal groups of the non-peptidyl polymer may be the same as or different from each other. For example, the non-peptide polymer may possess a maleimide group at one end and an aldehyde group, a propionaldehyde group or a butyraldehyde group at the other end. When a polyethylene glycol having a reactive hydroxy group at both ends thereof is used as the non-peptidyl polymer, the hydroxy group may be activated to various reactive groups by the known chemical reactions, or a polyethylene glycol having a commercially available modified reactive group may be used so as to prepare the human follicle-stimulating hormone conjugate of the present invention.

The long-acting human follicle-stimulating hormone formulation of the present invention maintains in vivo activity of human follicle-stimulating hormone, including stimulation of follicular production, development and maturation in females and sperm production in males, and also remarkably increases the serum half-life to improve in vivo duration of human follicle-stimulating hormone. Therefore, it can be used in the treatment of infertility, for example, in assisted reproductive technology, including in-vitro fertilization embryo transfer (IVF-ET), gamete intrafallopian transfer (GIFT), zygote intrafallopian transfer (ZIFT), and intra-cytoplasmic sperm injection (ICSI), or test-tube baby techniques, and for the treatment of anovulation, hypogonadotropic hypogonadism and polycystic ovary syndrome.

The long-acting formulation of the present invention has an excellent effect of maintaining in vivo duration and stability. In accordance with the specific Example of the present invention, the long-acting human follicle-stimulating hormone formulation of the present invention has approximately 10 fold-increase in the half-life, compared to the native human follicle-stimulating hormone (Table 2).

The long-acting formulation of the present invention may comprise a pharmaceutically acceptable carrier. For oral administration, the pharmaceutically acceptable carrier may include a binder, a lubricant, a disintegrator, an excipient, a solubilizer, a dispersing agent, a stabilizer, a suspending agent, a coloring agent, and a perfume. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, and a preserving agent.

The long-acting formulation of the present invention may be formulated into a variety of dosage forms in combination with the aforementioned pharmaceutically acceptable carriers. For example, for oral administration, the long-acting formulation may be formulated into tablets, troches, capsules, elixirs, suspensions, syrups or wafers. For injectable preparations, the long-acting formulation may be formulated into single-dose ampule or multidose container. The long-acting formulation may be also formulated into solutions, suspensions, tablets, pills, capsules and sustained release preparations.

Examples of the carrier, the excipient, and the diluent suitable for the formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the formulations may further include fillers, anticoagulating agents, lubricants, humectants, perfumes, and antiseptics.

The long-acting formulation according to the present invention is useful in the treatment of infertility, for example, assisted reproductive technology, including in-vitro fertilization embryo transfer (IVF-ET), gamete intrafallopian transfer (GIFT), zygote intrafallopian transfer (ZIFT), and intra-cytoplasmic sperm injection (ICSI), or test-tube baby techniques, and in the treatment of anovulation, hypogonadotropic hypogonadism and polycystic ovary syndrome, and thus these diseases can be treated by administration of the long-acting formulation.

The term "administration", as used herein, means introduction of a predetermined amount of a substance into a patient by a certain suitable method. The long-acting formulation of the present invention may be administered via any of the common routes, as long as it is able to reach a desired tissue. A variety of modes of administration are contemplated, including intraperitoneally, intravenously, intramuscularly, subcutaneously, intradermally, orally, topically, intranasally, intrapulmonarily and intrarectally, but the present invention is not limited to these exemplified modes of administration. However, since peptides are digested upon oral administration, active ingredients of a composition for oral administration should be coated or formulated for protection against degradation in the stomach.

Preferably, the long-acting formulation may be administered in an injectable form. In addition, the long-acting formulation of the present invention may be administered using a certain apparatus capable of transporting the active ingredients into a target cell.

The long-acting formulation of the present invention can be determined by several related factors including the types of diseases to be treated, administration routes, the patient's age, gender, weight and severity of the illness, as well as by the types of the drug as an active component. Since the pharmaceutical composition of the present invention has excellent in vivo duration and titer, it can remarkably reduce the administration frequency and dose of pharmaceutical drugs of the present invention.

In another aspect, the present invention provides a method for preparing a long-acting human follicle-stimulating hormone formulation, comprising the steps of:

(1) covalently linking an amine group or thiol group of human follicle-stimulating hormone with a non-peptidyl polymer having a reactive group selected from the group consisting of aldehyde, maleimide, and succinimide derivatives at both ends thereof;

(2) isolating a linker from the reaction mixture of (1), in which the linker comprises the human follicle-stimulating hormone covalently linked with the non-peptidyl polymer at a site other than the N-terminus; and (3) covalently linking an immunoglobulin Fc region to the other end of the non-peptidyl polymer of the isolated linker to produce a conjugate comprising the immunoglobulin Fc region and human follicle-stimulating hormone that are linked to each end of the non-peptidyl polymer.

The term "linker", as used herein, refers to an intermediate which is prepared by covalently linking the non-peptidyl polymer with human follicle-stimulating hormone. Afterward, an immunoglobulin Fc region is linked to the other end of the linker, namely the other end of the non-peptidyl polymer, to which human follicle-stimulating hormone is not linked.

In one preferred embodiment, the present invention provides a method for preparing a long-acting human follicle-stimulating hormone formulation, comprising the steps of:

(1) covalently linking a lysine group of human follicle-stimulating hormone with a non-peptidyl polymer having an aldehyde reactive group at both ends thereof;

(2) isolating a linker from the reaction mixture of (1), in which the linker comprises the human follicle-stimulating hormone covalently linked with the non-peptidyl polymer at its lysine residue; and (3) covalently linking an immunoglobulin Fc region to the other end of the non-peptidyl polymer of the isolated linker to produce a protein conjugate comprising the immunoglobulin Fc region and human follicle-stimulating hormone that are linked to each end of the non-peptidyl polymer. More preferably, the non-peptidyl polymer and the lysine residue of human follicle-stimulating hormone of (1) are linked at pH 7.5 or higher.

In another preferred embodiment, the present invention provides a method for preparing a long-acting human follicle-stimulating hormone formulation, comprising the steps of:

(1) covalently linking the N-terminal amino group of immunoglobulin Fc with two reactive terminal groups of non-peptidyl polymer having three reactive terminal groups;

(2) isolating a linker from the reaction mixture of (1), in which the linker comprises immunoglobulin Fc covalently linked with the non-peptidyl polymer; and (3) covalently linking human follicle-stimulating hormone to the other end of the non-peptidyl polymer of the isolated linker.

Further, in one preferred embodiment, the present invention provides a method for treating a subject having a reproduction disorder, the method comprising of administering to the subject an effective amount of the long-acting formulation. Preferably, the reproductive disorder is infertility.

Further, in one preferred embodiment, the present invention provides a method for increasing a subject's fertility, the method comprising administering an effective amount of the long-acting formulation.

As used herein, a subject can be a mammal, for example, human, a non-human primate, a horse, a sheep, a cat, a dog, a cow or a pig.

MODE FOR INVENTION

Hereinafter, a better understanding of the present invention may be obtained through the following Examples which are set forth to illustrate, but are not to be construed as the limit of the present invention.

Example 1

Production of Human Follicle-Stimulating Hormone

In order to produce human follicle-stimulating hormone, the cell line HMFS126 (KCTC11529BP) was cultured using serum-free medium in a 7.5 L animal cell bioreactor with a working volume of 5 L to produce human follicle-stimulating hormone. The production method will be briefly described. First, to obtain the number of cells required for the cultivation in the bioreactor, the frozen cell line was thawed, and cultured in a 250 ml Erlenmeyer flask using 30 ml of serum-free medium (EX-CELL CHO medium, SAFC, Cat.#63225C), and then subcultured every two days to increase the number of cells. The cells were inoculated into the bioreactor at a density of 10×105 cells/ml. The cells were cultured in the bioreactor using serum-free medium (EX-CELL CHO medium, SAFC, Cat.#63289C) by a continuous process at 37° C. until the number of cells increased to 100×105 cells/ml or more. Then, the temperature was decreased to 30.5° C., and 1 mM sodium butyrate (Sigma, Cat# B-5887) was added thereto, and the cells were cultured for 20 days to produce human follicle-stimulating hormone. While continuously feeding fresh serum-free media at a predetermined rate during the production period, the culture supernatant was collected from the reactor every 24 hrs, and recovered by centrifugation. Subsequently, the ultrafiltration membrane (SARTOCON Slice Cassette, PESU, Sartorius, MWCO 10K) was washed with 1 L of 1 N NaOH for 1 hr or longer, and finally rinsed with 5 L of distilled water. Human follicle-stimulating hormone-expressing culture media was applied thereto, and concentrated 20-fold. At this time, there was little loss of follicle-stimulating hormone, and the concentrated follicle-stimulating hormone was maintained at a final concentration of 0.1 mg/ml. The concentrated culture media were stored at −20° C. until each batch was completed, and then collected and purified.

Example 2

Dye Affinity Chromatography Step

For the dye affinity chromatography step, 1 M glycine/sodium hydroxide buffer (pH 9.0) was added to the concentrated human follicle-stimulating hormone culture media at a final concentration of 50 mM, and then 3.5 M potassium chloride solution was added at a final concentration of 0.2 M. The solution-added culture medium was finally filtered using a 0.45 μm filter (Sartopore 2300, Sterile Capsule, 0.8+0.45 μm), and applied to dye affinity chromatography. In the present invention, a blue sepharose fast flow (GE healthcare) resin-packed column was used for dye affinity chromatography, and proteins were eluted from the applied sample using equilibration and washing buffer A (50 mM glycine-sodium hydroxide–(pH 9.0)+0.2 M potassium chloride) and an elution buffer B (50 mM glycine-sodium hydroxide (pH 9.0)+2.5 M potassium chloride) by isocratic elution (FIG. 1).

Example 3

Hydrophobic Chromatography Step

Figure 2:
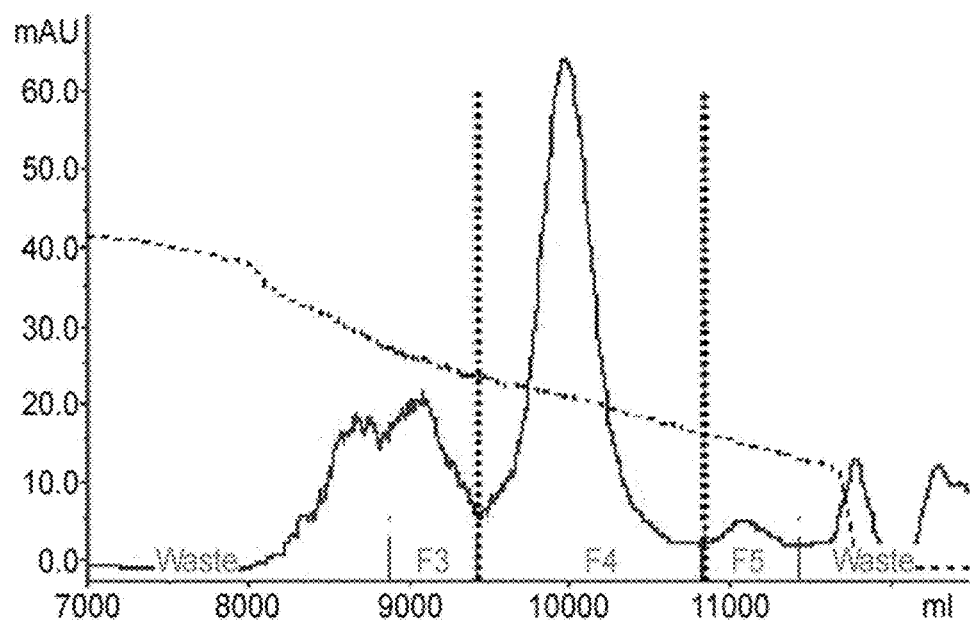
FIG. 2 is the result of hydrophobic chromatography for the purification of human FSH.

1 M Tris (pH 7.0) buffer was added to the sample eluted in the dye affinity chromatography step at a final concentration of 100 mM, and pH of the sample was approximately 8.0, and applied to hydrophobic chromatography. In the present invention, source 15 PHE (GE healthcare) resin-packed column was used for hydrophobic chromatography, and proteins were eluted from the applied sample with six column volumes of a linear gradient from solution A (10 mM Tris (pH 8.0)+1 M ammonium sulfate) to a solution B (10 mM Tris (pH 8.0)+ 20% isopropanol) (FIG. 2).

Example 4

Concentration and Diafiltration Step of Human FSH by Ultrafiltration

An ultrafiltration membrane (SARTOCON Slice Cassette, PESU, Sartorius, MWCO 10 K) was washed with 1 L of 1 N NaOH and 5 L of distilled water, and then a hydrophobic chromatography elution buffer was diluted 3-fold using a dilution buffer (10 mM ultrapolyphosphate (pH 8.0)), followed by concentration and diafiltration. The final diafiltration dilution was 1000-fold, and the final concentration of the concentrated human follicle-stimulating hormone was approximately 1 mg/ml, and for ultrafiltration, 10 K MWCO was used.

Example 5

Hydroxyapatite Chromatography Step

Figure 3:
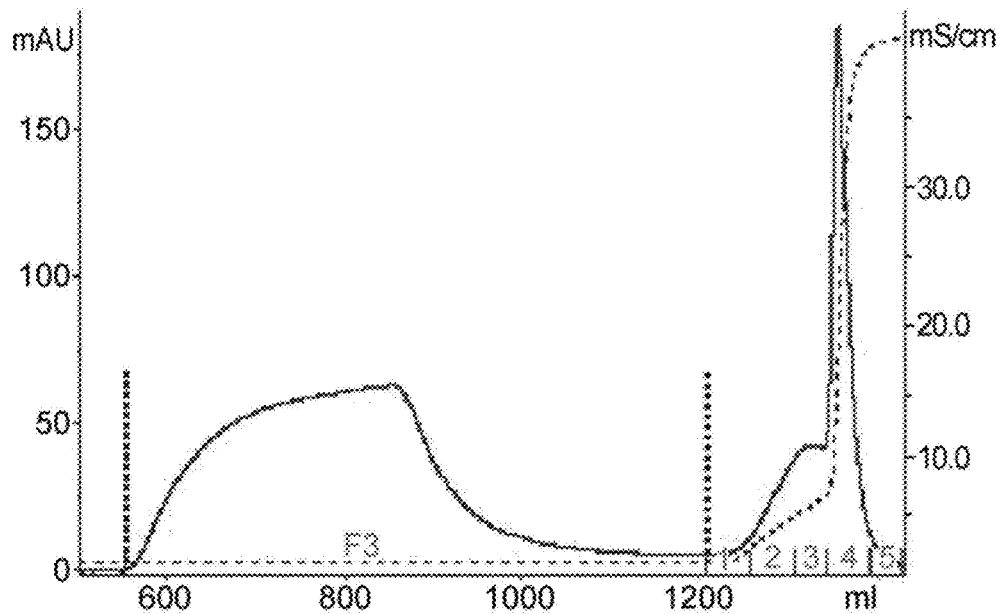
FIG. 3 is the result of hydroxyapatite chromatography for the purification of human FSH.

The sample that was concentrated by diafiltration using a 10 mM sodium phosphate (pH 8.0) solution to a concentration of 1 mg/ml was applied to ceramic hydroxyapatite chromatography. In the present invention, for hydroxyapatite chromatography, a macro-prep ceramic hydroxyapatite type 1 (80 μm, Bio-Rad) resin-packed column was used, and the concentrated sample was applied to a column equilibrated with a solution A (10 mM sodium phosphate (pH 8.0)). Thereafter, a human follicle-stimulating hormone-containing eluate was recovered in the flow-through fraction, and other proteins adsorbed to the column were eluted and removed using a solution B (500 mM sodium phosphate (pH 8.0)) (FIG. 3).

Example 6

Ultrafiltration and Ethanol Treatment Step

An ultrafiltration membrane (Pellicon2 PLCCC, Millipore, MWCO 5 K) was washed with 0.5 L of 0.1 N NaOH and 2 L of distilled water, and then human follicle-stimulating hormone obtained by hydroxyapatite chromatography was concentrated to a concentration of 2 mg/ml. The concentrated human follicle-stimulating hormone was mixed with an equal amount of a 100% ethanol solution, and incubated at room temperature. The incubation was performed under stirring at room temperature for 3 hrs under the conditions of 1 mg/ml concentration of follicle-stimulating hormone and 50% ethanol.

Example 7

Anion-Exchange Chromatography Step

Figure 4:
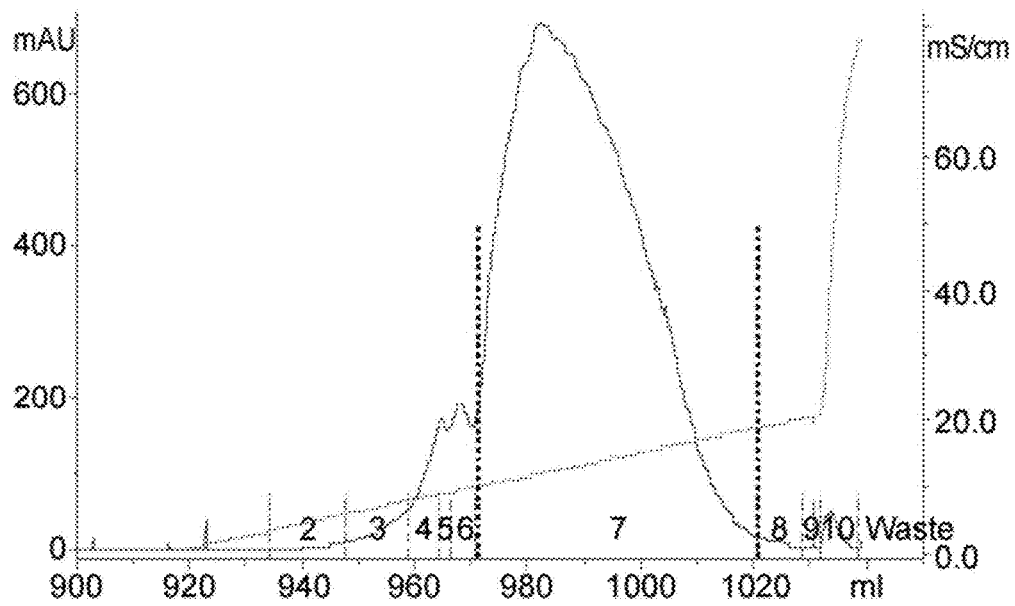
FIG. 4 is the result of anion-exchange chromatography for the purification of human FSH.

The human follicle-stimulating hormone treated with ethanol was buffer-exchanged using a 10 mM Tris (pH 7.5) buffer by size-exclusion chromatography, and applied to anion-exchange chromatography equilibrated with a solution A (10 mM Tris (pH 7.5)). For anion-exchange chromatography, a source 15Q (GE healthcare) resin-packed column was used, and proteins were eluted from the applied sample with ten column volumes of a linear gradient using solution A and solution B (10 mM Tris (pH 7.5)+1 M sodium chloride) to reach the concentration of solution B to 40% (FIG. 4).

Example 8

Analysis of Purified Human FSH

The human follicle-stimulating hormone purified by four-step column chromatography was analyzed according to the FSH test procedures registered in EP. The purity of human follicle-stimulating hormone was analyzed by size-exclusion chromatography (SEC, size-exclusion chromatography), polyacrylamide gel electrophoresis (SDS-PAGE), and identification of follicle-stimulating hormone was performed by reverse chromatography, immunoblotting, and mass spectrometry. Glycosylation was measured by isoelectric focusing (IEF). The quantification of host-derived DNA and protein was performed (FIG. 5).

Example 9

Pegylation and Purification of Human FSH

Figure 13:
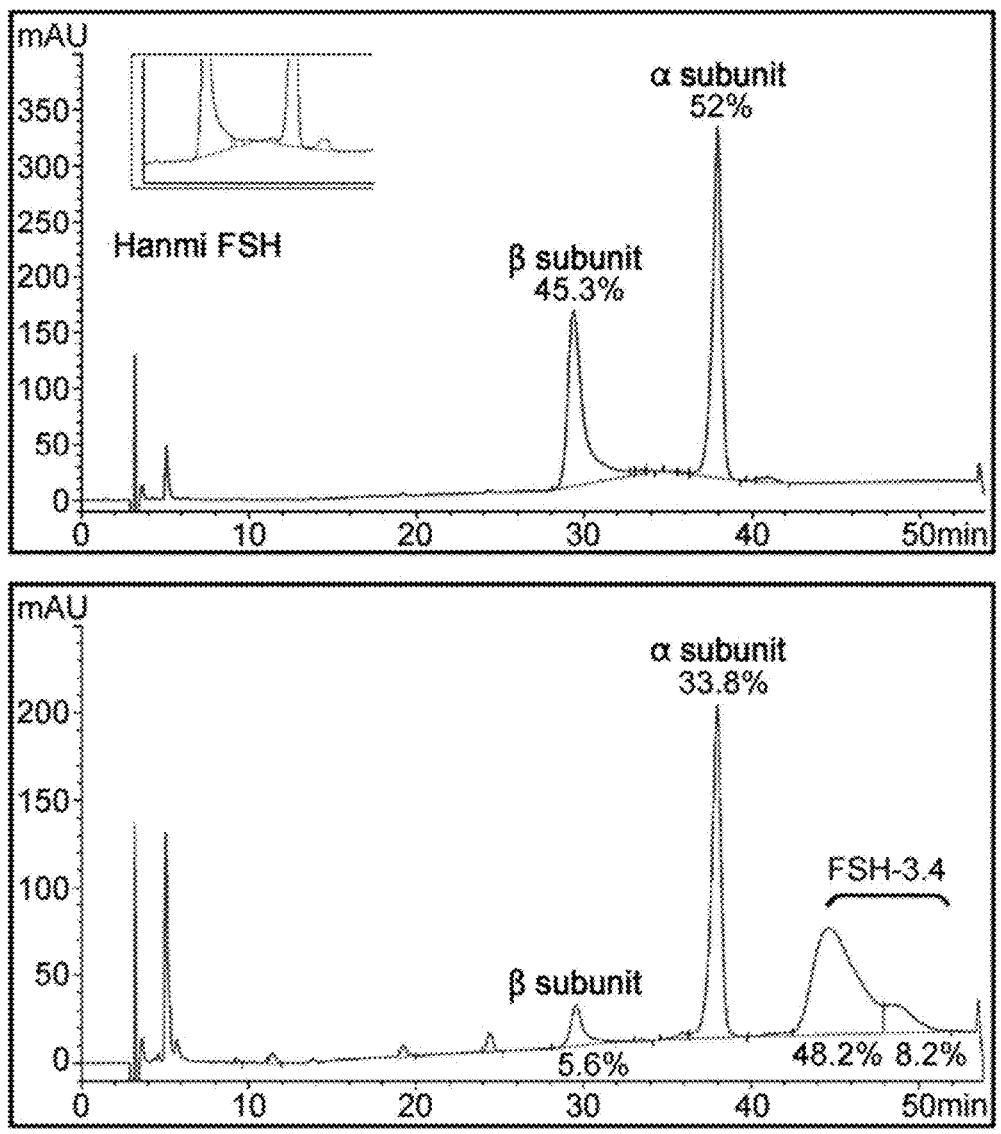
FIG. 13 is the result of analyzing 80% pegylation of the beta chain of human FSH using a reverse column.

For 80% or more pegylation of the beta chain of human follicle-stimulating hormone, 3.4 K PropionALD (2) PEG (PEG having two propionaldehyde groups, IDB Inc., Korea) and human follicle-stimulating hormone obtained in Example 7 and identified in Example 8 were subject to pegylation by reacting human follicle-stimulating hormone and PEG at 4° C. for 6 hrs and 30 min at a molar ratio of 1:15, with a protein concentration of 1.5 mg/ml. At this time, the reaction was performed in a 100 mM potassium phosphate buffer solution at pH 6.0, and 20 mM SCB (NaCNBH3) as a reducing agent was added thereto. A mono-pegylated peptide was purified from the reaction solution using SOURCE PHE (RESOURCE PHE 1 ml, Amersham Biosciences). The sample was bound to SOURCE PHE (RESOURCE PHE 1 ml, Amersham Biosciences) using 20 mM Tris (pH 7.5) and 0.7 M ammonium sulfate, and then the concentration of ammonium sulfate was gradually decreased and an organic solvent was added to elute the sample. Human follicle-stimulating hormone having a weak affinity to the HIC column was earlier eluted, and human follicle-stimulating hormone-3.4K PEG having a strong affinity to the HIC column was then eluted. Mono-pegylation of the eluted peaks was confirmed using a SDS-PAGE gel. To confirm 80% pegylation of B chain of human follicle-stimulating hormone, a reverse column was used, and the results are shown in FIG. 13.

Column: SOURCE PHE (RESOURCE PHE 1 ml, Amersham Biosciences)
Flow rate: 1.0 ml/min
Gradient: B 100→0% 100 min B (A: 20 mM Tris pH 8.0+0.7 M ammonium sulfate, B: 20 mM Tris pH8.0+20% isopropanol)

Example 10

Preparation of Human FSH-3.4K PEG-Immunoglobulin Fc Conjugate (HM12160A)

Using the same method as described in Example 9, 3.4K PropionALD(2) PEG and follicle-stimulating hormone were reacted, and then mono-pegylated follicle-stimulating hormone was only purified, and coupled with immunoglobulin Fc (Hanmi, Korea). The reaction was performed at a molar ratio of follicle-stimulating hormone-3.4K PEG:immunoglobulin Fc of 1:8.5 and a total concentration of protein of 40 mg/ml at 4° C. for 16 hours. The reaction was performed in a solution of 100 mM K-P (pH 6.0), and 20 mM SCB as a reducing agent was added thereto.

The coupling reaction solution was purified using two purification columns. First, Blue HP (HiTrap 5 ml, Amersham Biosciences) was used to remove a large amount of immunoglobulin Fc which had not participated in the coupling reaction. The immunoglobulin Fc having a weak affinity to Blue FF was eluted using 20 mM Tris (pH 7.5), and then the remaining immunoglobulin Fc was completely removed at a low concentration of salt and high pH (0.2 M KCl+50 mM Gly-NaOH pH 9.0). Then, the unreacted follicle-stimulating hormone-3.4K PEG and follicle-stimulating hormone-PEG-immunoglobulin Fc were eluted at a high concentration of salt and high pH (2.5 M KCl+50 mM Gly-NaOH pH 9.0).

By this primary purification procedure, immunoglobulin Fc was removed, but follicle-stimulating hormone-3.4K PEG and follicle-stimulating hormone-immunoglobulin Fc could not be completely separated from each other, since they have similar affinities.

Figure 6:
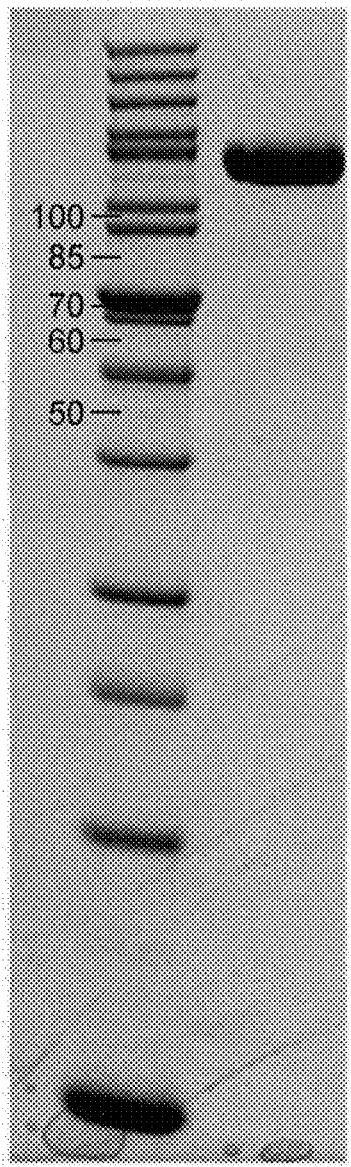
FIG. 6 is the result of analyzing human FSH-3.4K PEG-immunoglobulin Fc conjugate, which is prepared by using a non-peptidyl polymer having two reactive terminal groups.
Figure 7:
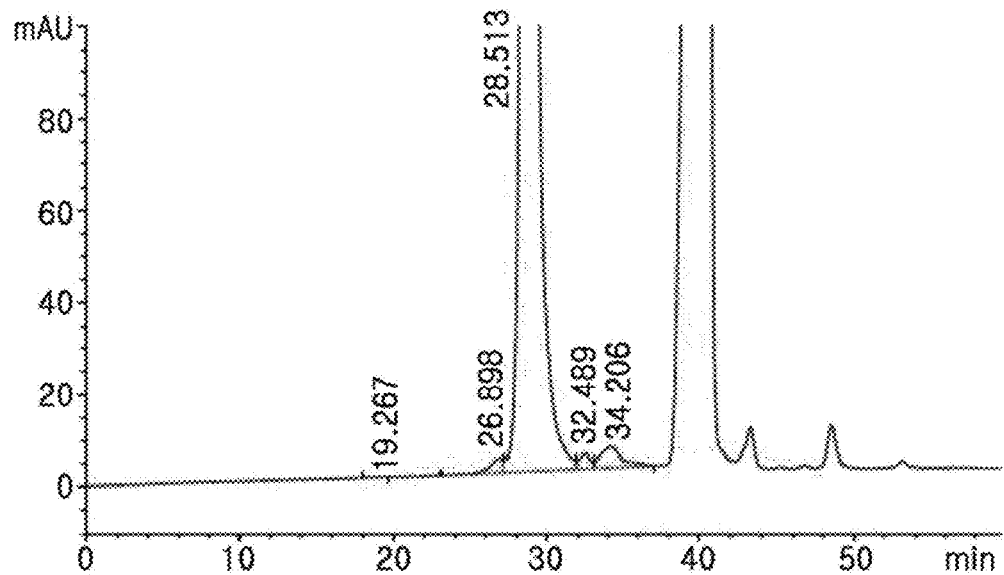
FIG. 7 is the result of size-exclusion chromatography for analyzing the purity of human FSH-3.4K PEG-immunoglobulin Fc conjugate, which is prepared by using a non-peptidyl polymer having two reactive terminal groups.

Accordingly, secondary purification was performed using hydrophobicity of two materials. 20 mM Tris (pH 7.5) and 1.3 M ammonium sulfate in SOURCE ISO (RESOURCE ISO 1 ml, Amersham Biosciences) were used. The follicle-stimulating hormone-3.4 K PEG having a weak affinity to HIC column was not bound to SOURCE ISO and eluted in 20 mM Tris (pH 7.5) and 1.3 M ammonium sulfate, and follicle-stimulating hormone-immunoglobulin Fc having a strong affinity was then eluted by gradually decreasing the concentration of ammonium sulfate. Since they have prominently different hydrophobicity, they can be more easily separated from each other than in the ion exchange column (FIG. 6). Purity of 97.66% was obtained from the HPLC size-exclusion chromatography analysis (FIG. 7).

Column: Blue HP (HiTrap 5 ml, Amersham Biosciences)
Flow rate: 3.0 ml/min
Gradient: A 0→100% 0 min B→100% 0 min C (A: 20 mM Tris pH 7.5, B: 50 mM glycine-sodium hydroxide pH 9.0+0.2 M potassium chloride, C: 50 mM glycine-sodium hydroxide pH 9.0+2.5 M potassium chloride)
Column: SOURCE ISO (RESOURCE ISO 1 ml, Amersham Biosciences)
Flow rate: 1.0 ml/min
Gradient: B 100→0% 100 min B (A: 20 mM Tris pH 7.5, B: A+1.3 M ammonium sulfate)

Example 11

Pegylation and Purification of Human FSH and Immunoglobulin Fc

5K PropionALD(3) PEG (PEG having three propionaldehyde groups, NOF., Japan) and both N-terminus of immunoglobulin Fc (Hanmi, Korea) were subject to pegylation by reacting protein and PEG at 4° C. for 4 hrs and 30 min at a molar ratio of 1:2 with a protein concentration of 6 mg/ml.

At this time, the reaction was performed in a 100 mM Potassium phosphate buffer at pH 6.0, and 20 mM SCB (NaCNBH3) as a reducing agent was added thereto.

A mono-pegylated peptide was purified from the reaction solution using SOURCE Q (FineLINE 1000 ml, Amersham Biosciences). Mono-pegylation of the eluted peaks was confirmed using a SDS-PAGE gel.

Column: SOURCE Q (FineLINE 1000 ml, Amersham Biosciences)
Flow rate: 40.0 ml/min
Gradient: A 0→4% 1 min B→24% 80 min B (A: 20 mM Tris pH 7.5, B: A+1 M NaCl)

Example 12

Preparation of Human FSH-5K PEG-Immunoglobulin Fc Conjugate (HM12160B)

Using the same method as described in Example 11, 5K PropionALD(3) PEG and both N-terminus of immunoglobulin Fc were reacted, and then mono-pegylated immunoglobulin Fc was only purified, and coupled with human follicle-stimulating hormone obtained in Example 7 and identified in Example 8. The reaction was performed at a molar ratio of human follicle-stimulating hormone:immunoglobulin Fc-5K PEG of 1:4.5 and a total concentration of protein of 40 mg/ml at 4° C. for 16 hours. The reaction was performed in a solution of 100 mM K-P (pH 6.0), and 20 mM SCB as a reducing agent was added thereto.

The coupling reaction solution was purified using two purification columns. First, Blue HP (Vantage L Laboratory Column 38 ml, Millipore) was used to remove a large amount of immunoglobulin Fc-5K PEG which had not participated in the coupling reaction. The immunoglobulin Fc-5K PEG having a weak affinity to Blue FF was eluted using 20 mM Tris (pH 7.5), and then remaining immunoglobulin Fc-5K PEG was completely removed at a low concentration of salt and high pH (0.2 M KCl+50 mM Gly-NaOH pH 9.0). Then, the unreacted human follicle-stimulating hormone and human follicle-stimulating hormone-PEG-immunoglobulin Fc were eluted at a high concentration of salt and high pH (2.5 M KCl+50 mM Gly-NaOH pH 9.0).

By this primary purification procedure, immunoglobulin Fc-5K PEG was removed, but FSH and FSH-immunoglobulin Fc could not be completely separated from each other, since they have similar affinities to the affinity column.

Figure 8:
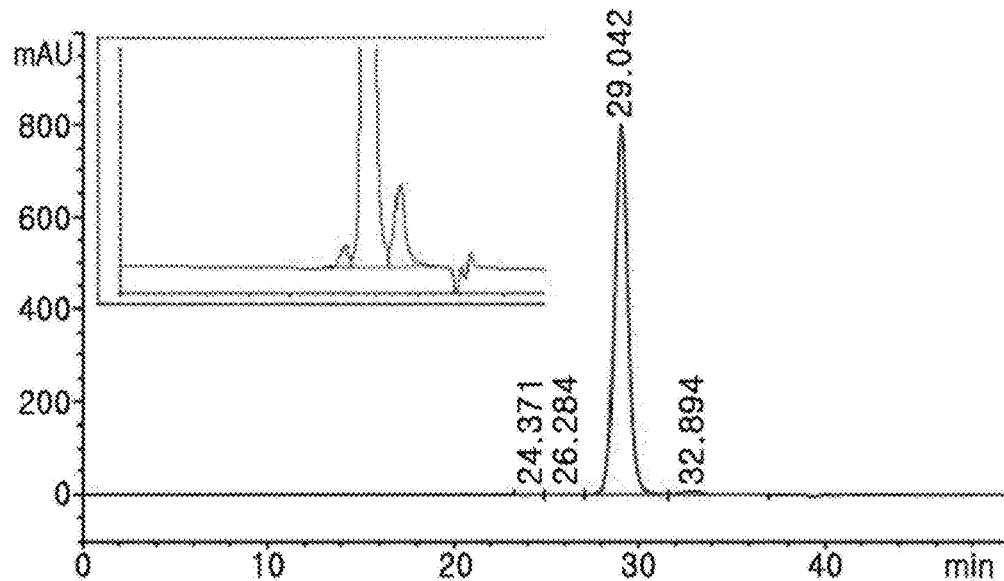
FIG. 8 is the result of size-exclusion chromatography for analyzing the purity of human FSH-3.4K PEG-immunoglobulin Fc conjugate, which is prepared by using a non-peptidyl polymer having three reactive terminal groups.

Accordingly, secondary purification was performed using hydrophobicity of two materials. The sample purified in the primary purification was bound using 20 mM Tris (pH 7.5) and 1 M ammonium sulfate in SOURCE PHE (XK 19 ml, AmershamBiosciences), and the sample was eluted by gradually decreasing the concentration of ammonium sulfate. The follicle-stimulating hormone having a weak affinity to HIC column was first eluted, and follicle-stimulating hormone-immunoglobulin Fc having a strong affinity was then eluted. Since they have prominently different hydrophobicity, they can be more easily separated from each other than in the ion exchange column. Purity of 98.07% was obtained from the HPLC size-exclusion chromatography analysis (FIG. 8).

Column: Blue FF (Vantage L Laboratory Column 38 ml, Millipore)
Flow rate: 5.0 ml/min
Gradient: A 0→100% 0 min B→100% 0 min C (A: 20 mM Tris pH 7.5, B: 50 mM glycine-sodium hydroxide pH 9.0+0.2 M potassium chloride, C: 50 mM glycine-sodium hydroxide pH 9.0+2.5 M potassium chloride)
Column: SOURCE PHE (XK 19 ml, Amersham Biosciences)
Flow rate: 2.0 ml/min
Gradient: B 100→0% 150 min B (A: 20 mM Tris pH 7.5, B: A+1 M ammonium sulfate)

Example 13

Comparison of In-vivo Efficacy between Long-Acting FSH and Native Human FSH

To test in-vivo efficacy of the long-acting human follicle-stimulating hormone formulation, the changes in ovary weight of immature female mice were analyzed. 21-day-old immature female mice were administered with the long-acting formulation at a dose of 0.5 or 1.5 mcg/head (based on FSH concentration) once for 3 days, and with native human follicle-stimulating hormone at a dose of 0.5 mcg/head every day or at a dose of 1.5 mcg/head once. During three experimental days, the human follicle-stimulating hormone formulation was co-administered with human chorionic gonadotropin at a dose of 13.3 IU/head every day. At this time, the used human follicle-stimulating hormone formulation was a long-acting formulation prepared by using the non-peptidyl polymer having two reactive terminal groups. 72 hrs after the initial injection of test material, the animals were euthanized, and the ovaries were excised and weighed. The single administration of long-acting human follicle-stimulating hormone formulation showed 26% increase in the ovary weight, compared to the equivalent dose of the native human follicle-stimulating hormone, and ⅓ dose thereof also showed an equal increase in the ovary weight (FIG. 9).

Example 14

Figure 10:
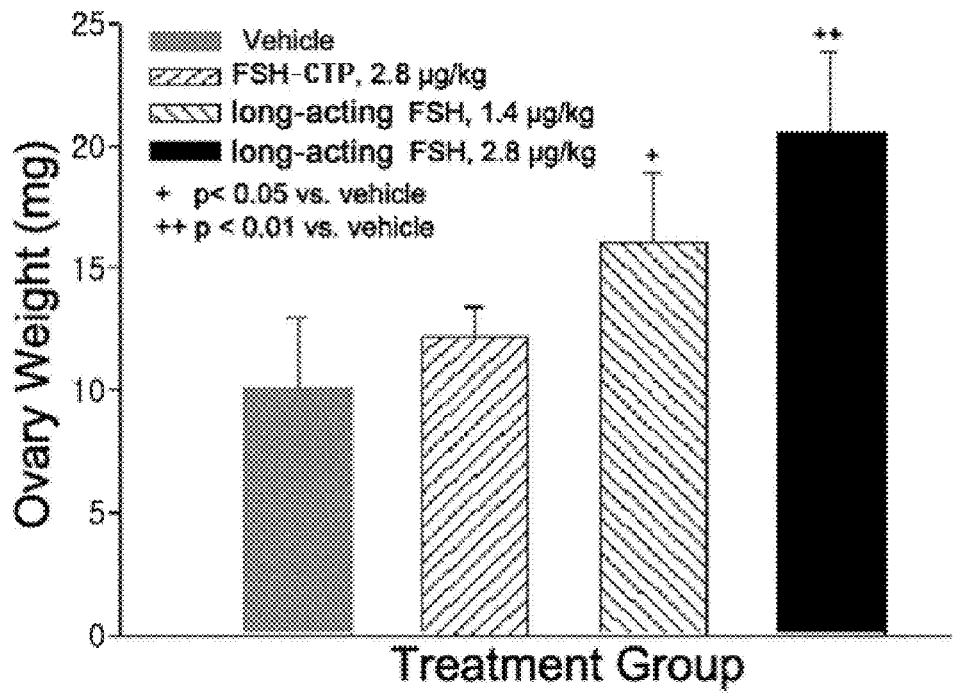
FIG. 10 is the result of comparison of in vivo efficacy between long-acting human FSH and human FSH-CTP fusion.

Comparison of In-vivo Efficacy between Long-Acting Human FSH and Human FSH-CTP Fusion To compare the in-vivo efficacy between long-acting human follicle-stimulating hormone formulation and human FSH-CTP fusion (Organon), an in-vivo efficacy test of human follicle-stimulating hormone formulation was performed according to the test procedures of Organon Inc., as follows. 21-day-old immature female mice were administered with the long-acting formulation at a dose of 1.4 or 2.8 mcg/head (based on hFSH concentration) once for 3 days, and administered with native human follicle-stimulating hormone at a dose of 2.8 mcg/head once. At this time, the used human follicle-stimulating hormone formulation was a long-acting formulation prepared by using the non-peptidyl polymer having two reactive terminal groups. Concomitant administration of human chorionic gonadotropin was not performed. 72 hrs after the initial injection of test material, the animals were euthanized, and the ovaries were excised and weighed. The increasing ratios of ovary weight in the long-acting formulation-treated groups were 38% and 68% in the ½ dose- and equivalent dose-treated groups, respectively, compared to the native human follicle-stimulating hormone-treated group. In the efficacy test of human FSH-CTP fusion, which was performed in the same manner as the above procedure, the increasing ratio of ovary weight in the human FSH-CTP fusion-treated group was 29% in the equivalent dose-treated group, compared to the native human follicle-stimulating hormone-treated group (Table 1), suggesting that the long-acting human follicle-stimulating hormone formulation of the present invention shows more excellent in-vivo efficacy (FIG. 10).

TABLE 1

| Parameters | HM12160A | FSH-CTP* |
|---|---|---|
| Dosage (mg/rat) | 1.4 | 2.8  2.8 |
| Increasing ratio of ovary weight (%) vs FSH | 31 | 68  29 |

*Hum Reprod, 2003; 18: 50-56

Example 15

Figure 11:
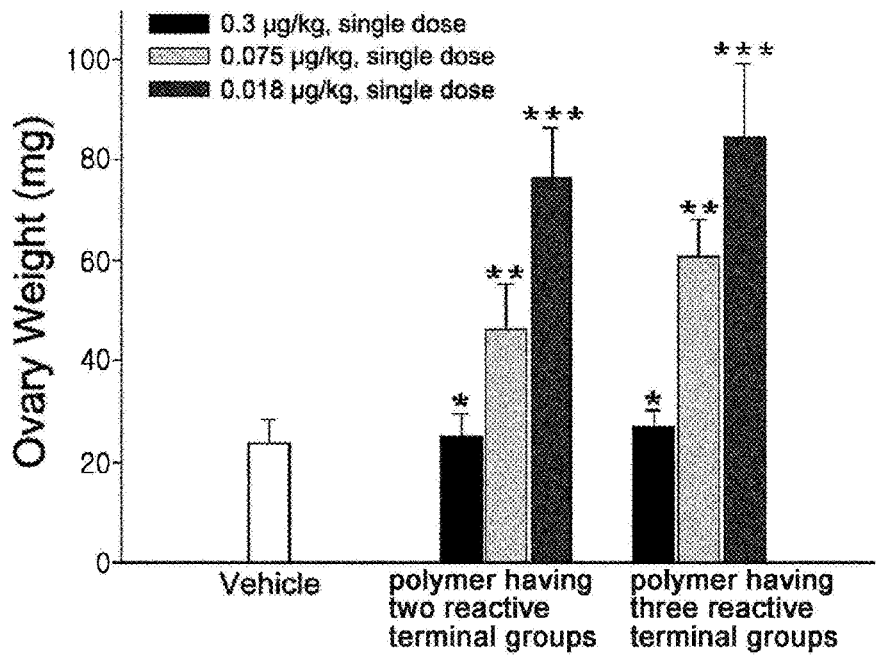
FIG. 11 is the result of comparison of in vivo efficacy between human FSH formulations, each of them prepared by using a polymer having two or three reactive terminal groups.

Comparison of In-vivo Efficacy between FSH Formulations Prepared Using Polymers Having Two and Three Reactive Terminal Groups To compare the in-vivo efficacy between long-acting human follicle-stimulating hormone formulations prepared by using different non-peptidyl polymers having two or three reactive terminal groups, the changes in ovary weight of immature female mice were analyzed. 21-day-old immature female mice were administered with each different long-acting formulation prepared by using non-peptidyl polymers having two or three reactive terminal groups at a dose of 0.3, 0.075, or 0.018 mcg/head (based on FSH concentration) once for 3 days. During three experimental days, human chorionic gonadotropin was co-administered with the long-acting human follicle-stimulating hormone formulation at a dose of 13.3 IU/head every day. 72 hrs after the initial injection of test material, the animals were euthanized, and the ovaries were excised and weighed. Upon single administration, both of two different long-acting human follicle-stimulating hormone formulations showed increased ovary weight in a dose-dependent manner, and there were no differences in ovary weight between formulations and between doses, indicating that the number of reactive terminal groups of non-peptidyl polymer does not affect the efficacy of the long-acting human follicle-stimulating hormone formulation (FIG. 11).

Example 16

In vivo Pharmacokinetic Analysis of Long-Acting Human FSH Formulation

Figure 12:
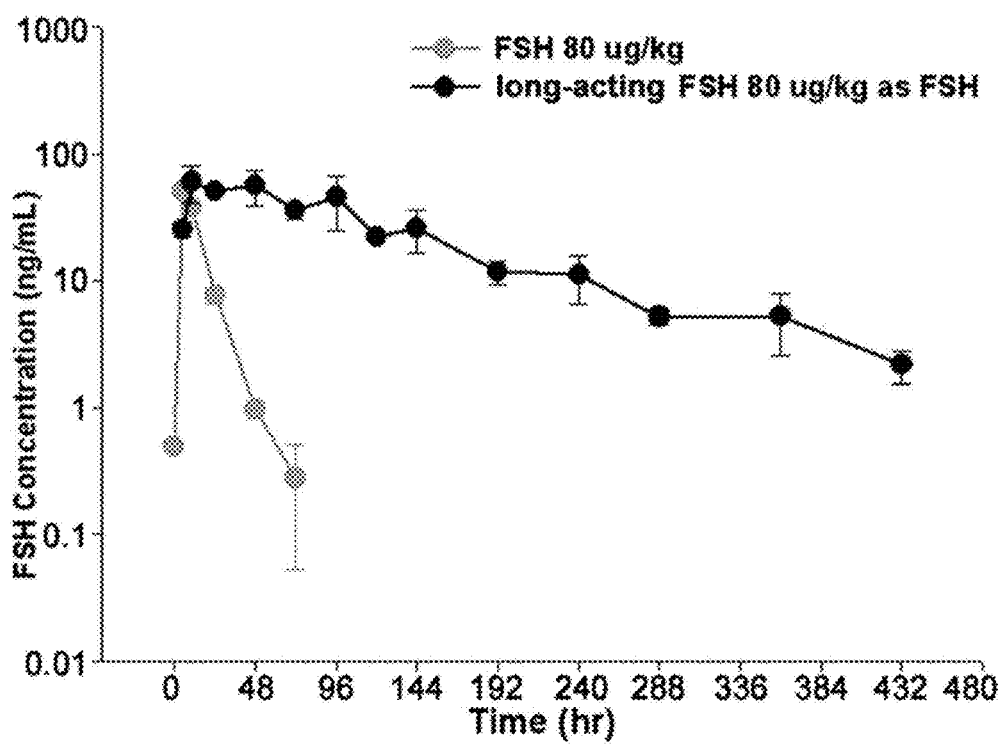
FIG. 12 is the result of in vivo pharmacokinetic analysis of long-acting human FSH formulation.

To test in vivo duration of the long-acting human follicle-stimulating hormone formulation, immature female mice were used to perform pharmacokinetic analysis. 21-day-old immature female mice were subcutaneously administered with native or long-acting human follicle-stimulating hormone at a dose of 80 g/kg (based on FSH concentration) once, and then time-dependent changes in serum level were measured using an ELISA kit, and pharmacokinetic parameters were calculated from the measured serum levels using Winnolin 5.2 software (Table 2). In this connection, the used human follicle-stimulating hormone was a long-acting formulation prepared by using non-peptidyl polymer having three reactive terminal groups. The half-life of human follicle-stimulating hormone was 85.6 hrs, which is 10-fold longer than the native human follicle-stimulating hormone (FIG. 12).

TABLE 2

| PK parameters | FSH | HM12160B |
|---|---|---|
| Dose (/kg as FSH) | 80 | 80 |
| T½ (hr) | 8.14 ± 1.92 | 85.62 ± 6.25 |

Example 17

Identification of Binding Site of FSH-3.4 K PEG-Immunoglobulin Fc Conjugate

Figure 14:
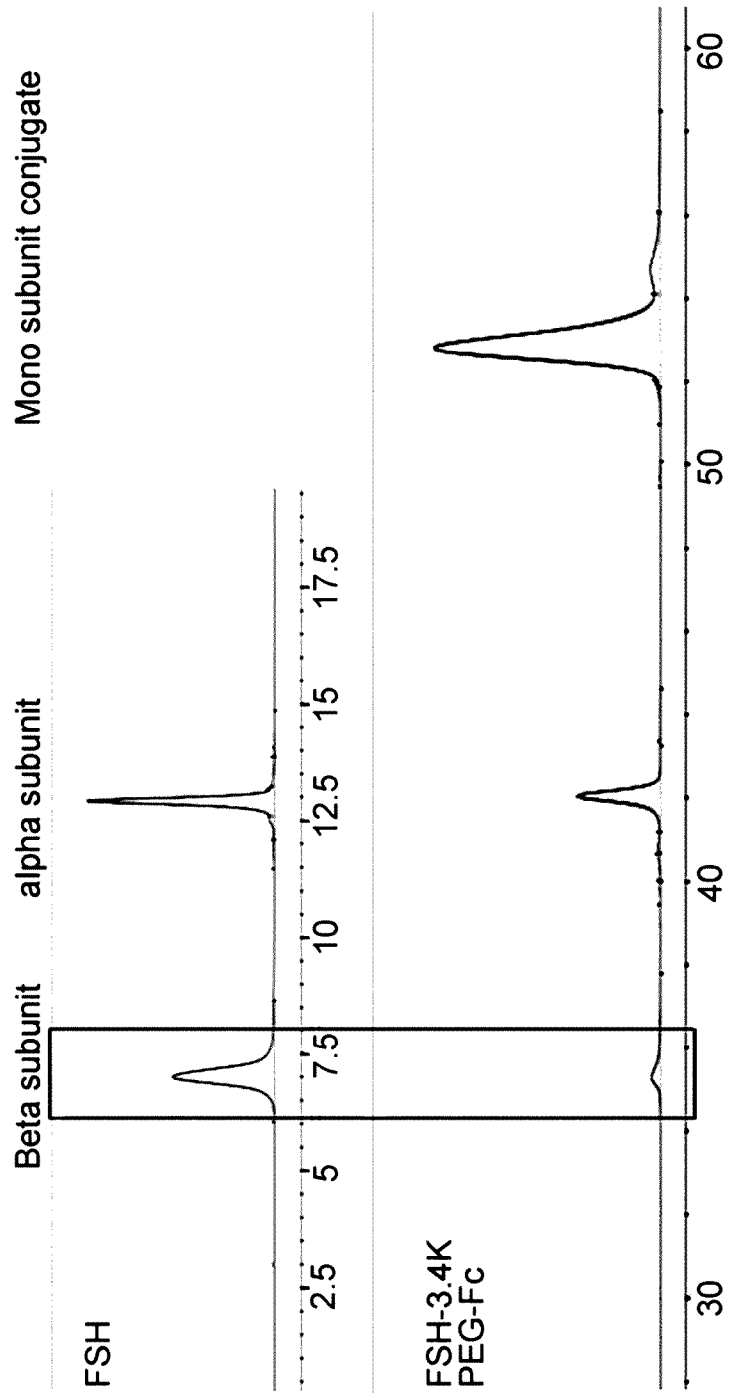
FIG. 14 is the result of analyzing binding to the beta subunit of human FSH.

In order to identify the binding site of human follicle-stimulating hormone-3.4 K PEG-immunoglobulin Fc conjugate, reverse HPLC chromatography was performed. Reverse chromatography was performed using 20 μg of human follicle-stimulating hormone (1 mg/ml) at low pH, and the result showed separation of alpha-subunit and beta-subunit. Under the same conditions, human follicle-stimulating hormone-3.4 K PEG-immunoglobulin Fc conjugate was also subjected to reverse chromatography, and the result showed that alpha- and beta-subunits unbound to 3.4 K PEG-immunoglobulin Fc and the subunits bound to 3.4K PEG-immunoglobulin Fc were separated. It was observed that the peak of beta-subunit of human follicle-stimulating hormone-3.4 K PEG-immunoglobulin Fc conjugate remarkably decreased, compared to that of human follicle-stimulating hormone (FIG. 14). Based on peak integration at 215 nm, 80% beta-subunit and 20% alpha-subunit were found to bind with 3.4 K PEG-immunoglobulin Fc.

The invention claimed is:

1. A long-acting human follicle-stimulating hormone formulation having improved in vivo duration and stability, comprising a human follicle-stimulating hormone conjugate consisting of human follicle-stimulating hormone linked to an immunoglobulin Fc region via a polyethylene glycol having a reactive terminal group,
   wherein the human follicle-stimulating hormone is comprised of an alpha-subunit and a beta-subunit;
   wherein the reactive terminal group of the polyethylene glycol is a propionaldehyde group; and
   wherein the polyethylene glycol is linked to the N-terminus of the beta-subunit of human follicle-stimulating hormone.

2. The long-acting human follicle-stimulating hormone formulation according to claim 1, wherein the non-peptidyl polymer has two reactive terminal groups, and each reactive terminal group of the non-peptidyl polymer is linked to an amine group or thiol group of the immunoglobulin Fc region and follicle-stimulating hormone, respectively.

3. The long-acting human follicle-stimulating hormone formulation according to claim 1, wherein the non-peptidyl polymer has three reactive terminal groups, and two of the three reactive terminal groups of the non-peptidyl polymer are linked to an amine group or thiol group of the immunoglobulin Fc region and human follicle-stimulating hormone, respectively.

4. The long-acting human follicle-stimulating hormone formulation according to claim 1, wherein the immunoglobulin Fc region is aglycosylated.

5. The long-acting human follicle-stimulating hormone formulation according to claim 1, wherein the immunoglobulin Fc region is composed of one to four domains selected from the group consisting of CH1, CH2, CH3 and CH4 domains.

6. The long-acting human follicle-stimulating hormone formulation according to claim 5, wherein the immunoglobulin Fc region further comprises a hinge region.

7. The long-acting human follicle-stimulating hormone formulation according to claim 1, wherein the immunoglobulin Fc region is an Fc region of an immunoglobulin selected from the group consisting of IgG, IgA, IgD, IgE, and IgM.

8. The long-acting human follicle-stimulating hormone formulation according to claim 7, wherein the immunoglobulin Fc region is a hybrid of domains of immunoglobulins of different classes selected from the group consisting of IgG, IgA, IgD, IgE, and IgM.

9. The long-acting human follicle-stimulating hormone formulation according to claim 7, wherein the immunoglobulin Fc region is in a form of a dimer or a multimer composed of single-chain immunoglobulins of a same class.

10. The long-acting human follicle-stimulating hormone formulation according to claim 7, wherein the immunoglobulin Fc region is an IgG4 Fc region.

11. The long-acting human follicle-stimulating hormone formulation according to claim 7, wherein the immunoglobulin Fc region is a human aglycosylated IgG4 Fc region.

12. The long-acting human follicle-stimulating hormone formulation according to claim 1, wherein the long-acting human follicle-stimulating hormone formulation is used in assisted reproductive technology for the treatment of infertility, said assisted reproductive technology being selected from the group consisting of in-vitro fertilization embryo transfer, gamete intrafallopian transfer, zygote intrafallopian transfer, intra-cytoplasmic sperm injection, and test-tube baby techniques.

13. The long-acting human follicle-stimulating hormone formulation according to claim 1, wherein the long-acting human follicle-stimulating hormone formulation is used for the treatment of hypogonadotropic hypogonadism or polycystic ovary syndrome.

14. A method for preparing the long-acting human follicle-stimulating hormone formulation of claim 1, comprising the steps of:
(1) covalently linking an amine group or thiol group of human follicle-stimulating hormone to a polyethylene glycol having a reactive terminal group at each end thereof, wherein said reactive terminal group is a propionaldehyde group;
(2) isolating a reaction product of step (1), wherein the reaction product comprises the human follicle-stimulating hormone covalently linked to one end of the polyethtylene glycol at the N-terminus of beta-subunit of the human follicle-stimulating hormone; and
(3) covalently linking an immunoglobulin Fc region to the other end of the polyethylene glycol of the isolated reaction product to produce a human follicle-stimulating hormone conjugate comprising the immunoglobulin Fc region and human follicle-stimulating hormone that are linked to each end of the polyethylene glycol.

15. A method for preparing the long-acting human follicle-stimulating hormone formulation of claim 1, comprising the steps of:
(1) covalently linking a lysine residue of human follicle-stimulating hormone to a non-peptidyl polymer having an aldehyde reactive group at both ends thereof at PH 7.5 or higher;
(2) isolating a reaction product of step (1), wherein the reaction product comprises the human follicle-stimulating hormone covalently linked to the non-peptidyl polymer at its lysine residue; and
(3) covalently linking an immunoglobulin Fc region to the other end of the non-peptidyl polymer of the isolated reaction product to produce a human follicle-stimulating hormone conjugate comprising the immunoglobulin Fc region and follicle-stimulating hormone that are linked to each end of the non-peptidyl polymer.

16. A method for preparing the long-acting human follicle-stimulating hormone formulation of claim 1, comprising the steps of:
(1) covalently linking the N-terminal amino group of immunoglobulin Fc to two reactive terminal groups of a polyethylene glycol having three reactive terminal groups;
(2) isolating a reaction product of step (1), wherein the reaction product comprises immunoglobulin Fc covalently linked to one end of the non-peptidyl polymer; and
(3) covalently linking human follicle-stimulating hormone to the other end of the polyethylene glycol of the isolated reaction product.

17. A method for treating a subject having a reproduction disorder, comprising administering to the subject an effective amount of the formulation of claim 1.

18. The method according to claim 17, wherein the reproductive disorder is infertility.

19. A method for increasing a subject's fertility, comprising administering to the subject an effective amount of the formulation of claim 1.

* * * * *